United States Patent [19]

Swoyer

[11] Patent Number: 5,683,445
[45] Date of Patent: Nov. 4, 1997

[54] MEDICAL ELECTRICAL LEAD

[76] Inventor: John M. Swoyer, 1440 147th Avenue Northwest, Andover, Minn. 55304

[21] Appl. No.: 639,458

[22] Filed: Apr. 29, 1996

[51] Int. Cl.$^6$ ............................................. A61N 1/05
[52] U.S. Cl. ................................. 607/125; 607/119
[58] Field of Search ................................ 128/642, 658; 607/115, 116, 119, 122, 125; 604/281

[56] References Cited

U.S. PATENT DOCUMENTS

| | | | |
|---|---|---|---|
| 3,729,008 | 4/1973 | Berkovitz. | |
| 4,317,458 | 3/1982 | Yokoyama | 607/122 |
| 4,402,328 | 9/1983 | Doring. | |
| 4,402,330 | 9/1983 | Lindemans. | |
| 4,407,304 | 10/1983 | Lieber et al. | 607/122 |
| 4,493,329 | 1/1985 | Crawford et al. | 607/125 |
| 4,552,157 | 11/1985 | Littleford | 607/125 |
| 4,699,157 | 10/1987 | Shonk | 607/122 |
| 4,777,955 | 10/1988 | Brayton et al. | 128/642 |
| 4,819,662 | 4/1989 | Heil, Jr. | 607/116 |
| 4,882,777 | 11/1989 | Narula | 607/122 |
| 5,170,787 | 12/1992 | Lindegren | 607/116 |
| 5,215,540 | 6/1993 | Anderhub | 604/281 |
| 5,304,139 | 4/1994 | Adams et al.. | |
| 5,306,263 | 4/1994 | Voda | 128/658 |
| 5,322,509 | 6/1994 | Rickerd | 604/280 |
| 5,383,922 | 1/1995 | Zipes et al. | 607/122 |
| 5,423,772 | 6/1995 | Lurie et al.. | |
| 5,462,545 | 10/1995 | Wang et al. | 607/122 |

FOREIGN PATENT DOCUMENTS 9320750 10/1993 WIPO ................................. 607/122

OTHER PUBLICATIONS

Abstract: Pacing and Clinical Electrophysiology; NASPE, Apr. 1995, vol. 18, No. 4, Part II, "Experience with a New Coronary Sinus Lead Specifically Designed for Permanent Left Atrial Pacing", Dubert et al.

*Primary Examiner*—William E. Kamm
*Assistant Examiner*—George R. Evanisko
*Attorney, Agent, or Firm*—Harold Patton; Michael J. Jaro

[57] ABSTRACT

A transvenous bipolar lead specifically designed for coronary sinus implantation. The lead has essentially two main characteristics, the distal end has a 45-degree pre-shape to facilitate introduction of the lead through a catheter and provide optimal positioning of the lead within the coronary sinus. The lead further features a distal electrode tip which itself is canted at an angle of 45 degrees on the distal end of the lead to provide a very close contact with the coronary sinus upper wall and, thus, with the left atrium inferolateral wall. In addition, each of these sections is flexible to permit the lead to be introduced through a relatively small-sized guide catheter. Finally, the lead further features a center lumen to also permit the lead to be straightened for introduction with a stylet.

14 Claims, 4 Drawing Sheets

MEDICAL ELECTRICAL LEAD

FIELD OF THE INVENTION

This invention relates to the field of body implantable medical device systems, and in particular to a body implantable medical device system which includes a medical electrical lead particularly designed for implantation into the coronary sinus.

BACKGROUND OF THE INVENTION

Modern electrical therapeutic and diagnostic devices for the heart, such as pacemakers, cardioverters, and defibrillators, for example, require a reliable electrical connection between the device and a region of the heart. Typically, a medical electrical "lead" is used for the desired electrical connection.

One type of commonly used implantable lead is a transvenous lead. Transvenous leads are positioned through the venous system to attach or electrically connect at their distal end to the heart. At their proximal end, they are connected to typically an implantable pulse generator. Such leads normally took the form of a long, generally straight, flexible, insulated conductor. Among the many advantages of a transvenous lead is that it permits an electrical contact with the heart without physically exposing the heart itself, i.e., major thoracic surgery is not required.

The specific design of a transvenous lead used is often varied depending upon the region of the heart to which it is to be connected. For example, U.S. Pat. No. 4,402,330 of Lindemans discloses a body implantable lead in which the lead body has a J-curve and the distal electrode has a permanent bend. In such a manner, the lead is configured to electrically connect to the right atrium.

While such a lead has been found acceptable for electrically connecting and thus pacing the right atrium, the need exists for a transvenous medical electrical lead which may provide an electrical connection to the left atrium. Of course the left atrium cannot, at present, be transvenously accessed with a lead for chronic implantation due to the direction of blood flow and the present limitations of materials. To be precise, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of the heart's hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the heart. For example, in patients with dilated cardiomyopathy, electrical stimulation of both the right side and the left side of the heart has been shown to be of major importance to improve the patient's well-being and manage heart failure. See, for example, Cazeau et al., "Four Chamber Pacing in Dilated Cardiomyopathy," PACE, November 1994, pgs. 1974–79. See also Brecker and Fontainem, St. et al., "Effects Of Dual Chamber Pacing With Short Atrioventricular Delay In Dilated Cardiomyopathy," Lancet November 1992 Vol. 340 p1308–1312; Xiao HB et al., "Effect Of Left Bundle Branch Block On Diastolic Function In Dilated Cardiomyopathy," Br. Heart J 1991, 66(6) p 443–447; and Fontaine, G. et al, "Electrophysiology Of Pseudofunction," CI.Meere (ed) Cardiac pacing, state of the art 1979, Pacesymp, 1979 Montreal.

At present there are several techniques for implanting a lead onto or into the left side of the heart. First, of course, is through general thoracic surgery; either via a median sternotomy; intercostal approach; or, in a more limited procedure, a sub-xiphoid approach. These procedures, however, involve major surgery which may be painful and dangerous for the patient, as well as extremely costly. The sub-xiphoid approach, moreover, only permits limited access to the anterolateral surface of the left ventricle and does not provide any access to the left atrium. Another approach used is to electrically access the left atrium is through the coronary sinus.

The coronary sinus, however, presents challenges in both implanting the lead in the proper position as well as ensuring the lead maintains sufficient electrical contact with the desired tissue. U.S. Pat. No. 5,423,772 of Lurie et al. discloses a coronary sinus catheter having three sections. Each section has varying degrees of flexibility, with the proximal reinforced section being stiffer than an intermediate section, the intermediate section being stiffer than the softened tip section. The catheter also is curved, with the curve beginning in the intermediate section, the curve further continuing into the softened tip section, where the radius of curvature decreases, i.e., the catheter becomes more curved closer to the tip. One drawback to such a design, however, is that the particular shape of the curve is not ideally suited for electrically accessing the left atrium. In addition, such a catheter is relatively complicated to manufacture due to the required reinforcing braid or other mends in the proximal reinforced section. Finally, such a catheter does not permit introduction of a stylet to assist in the placement of the catheter into the coronary sinus.

It is thus an object of the present invention to provide a medical electrical lead which is suitably shaped to provide an electrical connection through the coronary sinus to the left atrium.

A still further object of the present invention is to provide such a medical electrical lead which may be readily flexed during implantation to provide the ability to be introduced transvenously.

A still further object of the present invention is to provide a medical electrical lead having a pre-bent portion along the lead body which may be readily straightened through use of a stylet and which further includes a pre-bent portion at the electrode tip so that the electrode tip is properly oriented to the coronary sinus upper wall and, thus, with the left atrium inferolateral wall.

SUMMARY OF THE INVENTION

These and other objects are accomplished through the present invention. In one embodiment, the present invention comprises a transvenous bipolar lead specifically designed for coronary sinus implantation. The lead has essentially two main characteristics, the distal end has a 45-degree pre-shape to facilitate introduction of the lead through a catheter and provide optimal positioning of the lead within the coronary sinus. The lead further features a distal electrode tip which itself is canted at an angle of 45 degrees on the distal end of the lead to provide a very close contact with the coronary sinus upper wall and, thus, with the left atrium inferolateral wall. In addition, each of these sections is flexible to permit the lead to be introduced through a relatively small-sized guide catheter. Finally, the lead further features a center lumen to also permit the lead to be straightened for introduction with a stylet.

BRIEF DESCRIPTION OF THE DRAWINGS

The present invention may be better understood and appreciated with reference to a detailed description of the specific embodiment of the invention, when read in conjunction with the accompanying drawings, wherein.

It should be understood the drawings are not necessarily to scale.

DETAILED DESCRIPTION OF THE INVENTION

Figure 1:
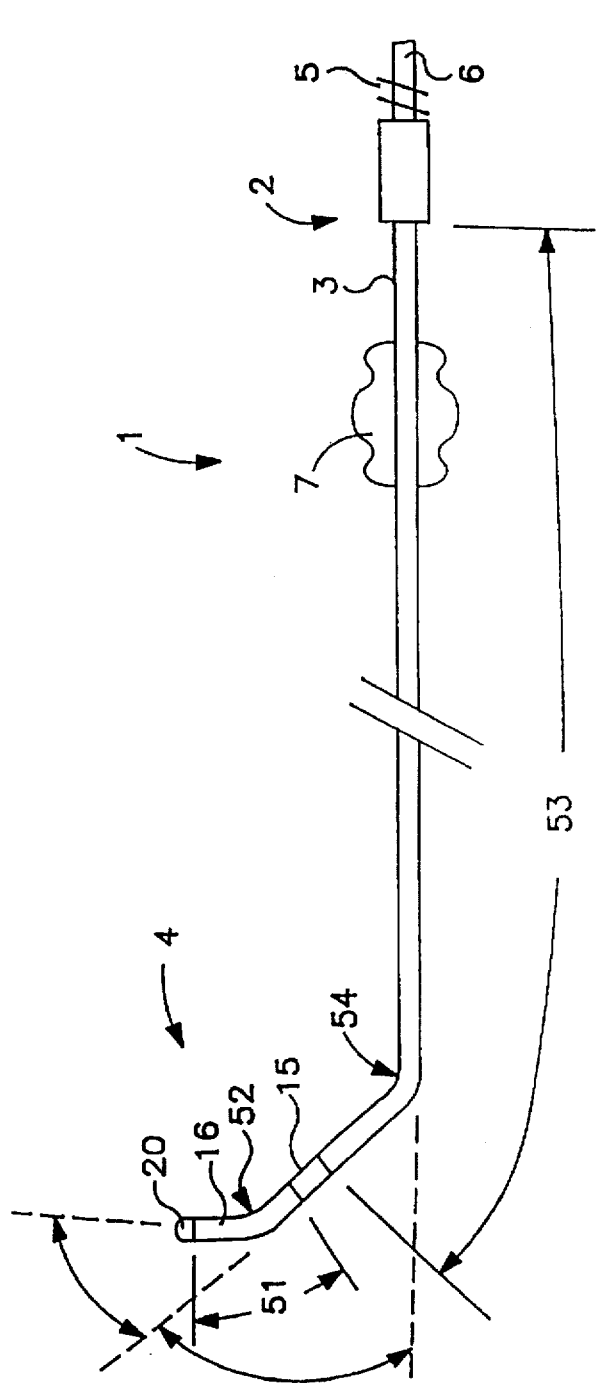
FIG. 1 is a plan view of the lead of the present invention.

Turning now to FIG. 1, which is a plan view of the lead of the present invention. As seen lead 1 consists essentially of three portions, connector assembly 2, lead body 3, and distal electrode assembly 4. Connector assembly 2 is constructed to meet the industry standard IS-1 Bi, although other types of connectors could be used, depending on the type of lead (e.g. unipolar) and its use (e.g. temporary.) As seen, connector assembly 2 has sealing rings 5 and connector pin 6, all of the type known in the art.

An anchoring sleeve 7 may also be provided for suturing the lead to body tissue. Anchoring sleeve 7 and connector assembly 2 are preferably fabricated from silicone, although they may also be constructed of any other suitable biocompatible material known in the art, such as polyurethane.

Connector pin 6 preferably has a lumen therethrough which corresponds to a lumen within the lead, as discussed below, to permit the introduction of a stylet into the lead and thereby impart stiffness.

Figure 2:
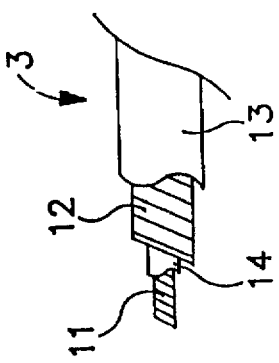
FIG. 2 is a fragmented detail of the construction of the lead body.

As best seen in FIG. 2, lead body 3 consists of two coiled conductors and two insulating sleeves. In particular, inner conductor 11 is disposed within and electrically insulated by inner sleeve 14. Outer conductor 12 is positioned concentric about inner sleeve 14 and inner conductor 11. Outer sleeve 13 is further positioned concentric over inner sleeve 14, inner conductor 11, and outer conductor 12. Sleeves are preferably constructed from polyurethane, although they may be constructed from any other bio-compatible material known in the art, such as silicone. Conductors are preferably multifilar coils and preferably are constructed from a body compatible alloy, such as MP35N.

Lead body 3 has essentially two sections. First section 51 extends between ring electrode 15 and tip electrode 20. Second section 53 extends from connector assembly 2 to ring electrode 15. Second section 53 is less stiff than first section 51. As seen in FIG. 1, first bend 52 located along first section 51, while second bend 54 is located along second section 53.

Figure 3:
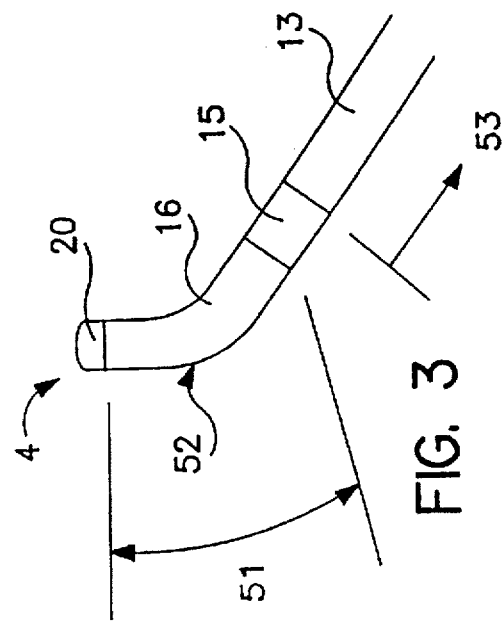
FIG. 3 is a detailed view of the distal end of the lead shown in FIG. 1.

Turning now to FIG. 3 which shows a detailed view of the distal end of the lead shown in FIG. 1. As seen, first section 51 of lead body 3 is pre-shaped to be canted between 15 and 90 degrees, with 45 degrees preferred, relative to the prior second section 53 of lead body. Pre-shape cant or bend 52 is provided to this section of lead body 3 through the TR (tip to ring) spacer 16 covering the conductor in this section of the lead body 3. This canting or pre-shape bend near the electrode tip, in conjunction with the pre-shape bend 54 within second section 54 of the lead body 3 permits the electrode tip to come in very close contact with the coronary sinus upper wall and, thus, with the left atrium inferolateral wall. As also seen, has second section 53 has a pre-shape bend 54 of between 15 and 90 degrees, with 45 degrees preferred, relative to the more proximal section of lead body 3. Second pre-shape bend 54 (see in FIG. 1) is provided to lead body 3 through inner sleeve 14, outer sleeve 13 and conductor 12. Second pre-shape bend 54, however, is of a small enough bias such that introduction of a straight stylet into the center lumen of the lead body 3 or the insertion of lead body 3 into a guide catheter (both discussed below) may cause the bend to be straightened. Although depicted as being within the same plane, it should be understood the above-described pre-shape bends may also be in different planes.

Figure 4:
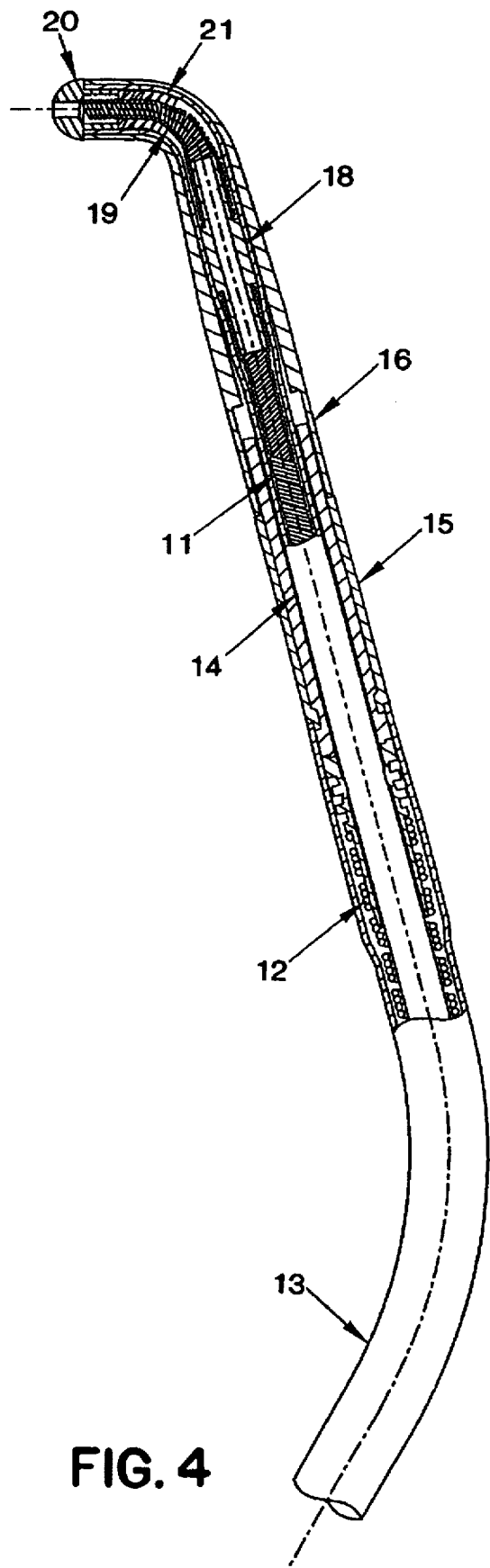
FIG. 4 is a cross sectional view of the distal end of the lead shown in FIG. 3.

FIG. 4 is a cross sectional view of the distal end of the lead shown in FIG, 3. As seen, outer sleeve 13 covers outer coil 12. Outer sleeve 13 and outer coil 12 are fashioned to provide the pre-bend to this section of lead body 3, discussed above. Outer coil 12 couples with ring electrode 15. Ring electrode 15 is preferably a polished platinum alloy, although other materials may also be used. Butted against the distal end of ring electrode 15 is TR spacer 16. TR (tip to ring) spacer 16 covers, in part, inner coil 17. Inner conductor is crimped into shank 18. Shank 18, in turn, is distally crimped into tip coil 19. Shank 18 is preferably an electrical conductor, such as MP35N as is tip coil 19. Tip coil 19 is electrically couple to tip electrode 20. Although tip electrode 20 is preferably positioned at the distal end of lead body 3, it may also be positioned off-set on lead body 3, such that it is positioned along only one side of lead body 3. Tip electrode 20 is preferable a hemispherical porous platinized electrode, such as the Medtronic CapSure SP although other types of electrodes may be used. In addition, it should be understood that other materials other than platinum may be used for both tip electrode 20 and ring electrode 15 including any conductive material from the class of materials consisting essentially of platinum, palladium, titanium, tantalum, rhodium, iridium, carbon, vitreous carbon and alloys, oxides or nitrides of such metals. Located within a hollow of tip electrode 20 is a monolithic controlled release device ("MCRD") 21. In the preferred embodiment, MCRD is loaded with a drug or pharmaceutical agent, such as the sodium salt of dexamethasone phosphate, to provide therapeutic dosage to the tissue immediately adjacent tip electrode.

Figure 5:
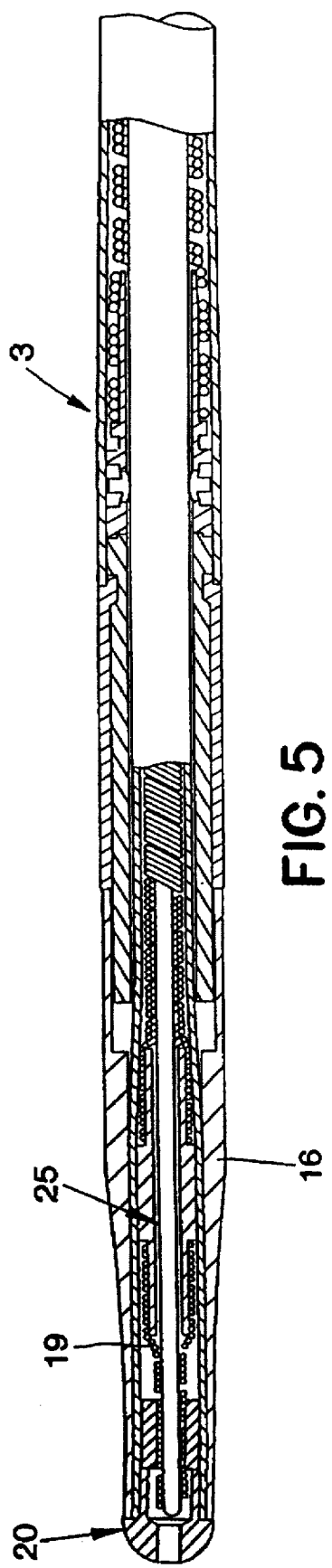
FIG. 5 is a cross sectional view of the distal end of the lead shown in FIG. 3 having a stylet inserted through the center lumen and the lead straightened.

One important aspect of the present invention is that the tip electrode 20 is biased relative to the lead body 3, but which may be straightened merely with a stylet. As best seen in FIG. 5, stylet 25 through the center lumen of lead body 3 causes the lead body 3 to become relatively straight.

Another important aspect of the present invention is that the lead body 3 has varying degrees of flexibility along its length. In particular, first section 51 of lead body 3 between ring electrode 15 and tip electrode 20 has a first degree of flexibility while second section 53 of lead body 3 between connector assembly 2 and ring electrode 15 has a second degree of flexibility. The first degree of flexibility is less than the second degree of flexibility.

Still another important aspect of the present invention is the location of the bends along the lead body 3. In particular, the first or more distal bend located between connector assembly 2 and ring electrode 15 is preferably located 1.15 inches from the tip electrode 20, although it may conceivably be located anywhere between 0.75 to 2 inches from the tip electrode 20. The second or more proximal bend located between ring electrode 15 and tip electrode 20 is preferably located 0.25 inches from the tip electrode 20, although it may conceivably be located anywhere between 0.10 to 0.40 inches from the tip electrode 20.

The above are important aspects because, taken together, they are intended to anchor or wedge the lead into position within the coronary sinus. This more distal bend, moreover, is intended to angle the tip electrode 20 towards the tissue to be stimulated. Both bends, however, occur over a uniform area.

Figure 6:
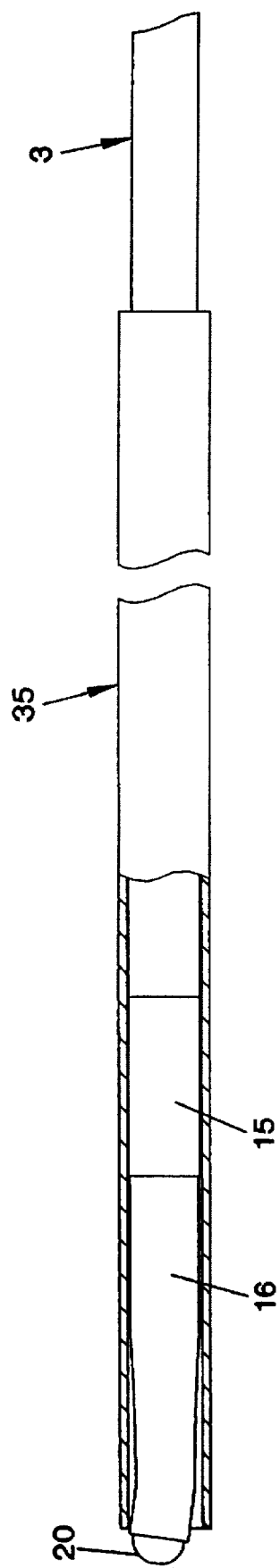
FIG. 6 is a partial sectional view of the distal end of the lead shown in FIG. 3 having been inserted into a guide catheter, thereby causing the distal end to become relatively less bent.

FIG. 6 is a partial sectional view of the distal end of the lead shown in FIG. 3 having been inserted into a guide catheter 35, thereby causing the distal end to become relatively less bent. As seen guide catheter 35 is used to deliver lead 1 to the desired location within the body. Guide catheter 35 may be any acceptable, guide catheter 35 preferably having a stiffness which is greater than the stiffness of either bend along lead body 3. Guide catheter 35, moreover, may be either substantially straight along its length of have one or more bends. Overall, the ability of lead 1 to be relatively straightened within guide catheter 35 so as to be precisely delivered into a location within the body is another important aspect of the present invention.

It is to be understood that the present invention is not limited to use only in pacing leads, and may be employed in the construction of may of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead comprising:

a connector assembly;

a lead body coupled to the connector assembly, the lead body having a first distal section and a second proximal section, the first section having a flexible first bend and a first stiffness, the second section having a flexible second bend and a second stiffness, the first stiffness greater than the second stiffness, second bend is between 15 to 90 degrees, the first bend is between 15 to 90 degrees; and a tip electrode coupled to the lead body.

2. The lead according to claim 1 wherein first bend is located 0.25 inches from the tip electrode.

3. The lead according to claim 1 wherein the second bend is located 1.15 inches from the tip electrode.

4. The lead according to claim 1 wherein the first bend and the second bend are in the same plane.

5. The lead according to claim 1 wherein the lead body further comprises a second conductor covered by a second insulative sheath, a ring electrode coupled to the second conductor, the ring electrode positioned along the lead body between the first section and the second section.

6. The lead according to claim 1 wherein the surface of the tip electrode exposed to the body is generally hemispherical in shape.

7. The lead according to claim 1 wherein the electrode is formed of porous metallic or other conductive materials from the class of materials consisting essentially of platinum, palladium, titanium, tantalum, rhodium, iridium, carbon, vitreous carbon and alloys, oxides and nitrides of such metals or other conductive materials.

8. A system for implanting a medical electrical lead comprising:

a guide catheter, the guide catheter having a lumen therethrough, the guide catheter having a guide catheter bend and a guide catheter stiffness; and a medical electrical lead disposed through the lumen of the guide catheter, the medical electrical lead having a connector assembly, a lead body coupled to the connector assembly, the lead body having a second proximal section and a first distal section, the first section having a flexible first bend and a first stiffness, the second section having a flexible second bend and a second stiffness, the first stiffness greater than the second stiffness, the first stiffness and the second stiffness less than the guide catheter stiffness, the second bend is between 15 to 90 degrees, the first bend is between 15 to 90 degrees, a tip electrode coupled to the lead body.

9. The system for implanting a medical electrical lead according to claim 8 wherein the guide catheter bend is substantially linear.

10. The system for implanting a medical electrical lead according to claim 8 wherein first bend is located 0.25 inches from the tip electrode.

11. The system for implanting a medical electrical lead according to claim 8 wherein the second bend is located 1.15 inches from the tip electrode.

12. The system for implanting a medical electrical lead according to claim 8 wherein the first bend and the second bend are in the same plane.

13. The system for implanting a medical electrical lead according to claim 8 wherein the system for implanting a medical electrical body further comprises a second conductor covered by a second insulative sheath, a ring electrode coupled to the second conductor, the ring electrode positioned along the lead for implanting a medical electrical body between the first section and the second section.

14. The system for implanting a medical electrical lead according to claim 8 wherein the surface of the tip electrode exposed to the body is generally hemispherical in shape.

* * * * *